United States Patent
Frazier

(10) Patent No.: US 6,755,586 B1
(45) Date of Patent: Jun. 29, 2004

(54) LIQUID APPLICATOR WITH SLIDE RING ACTIVATOR TOOL

(76) Inventor: Thomas G. Frazier, 17 Welden Dr., Doylestown, PA (US) 18901

( * ) Notice: Subject to any disclaimer, the term of this patent is extended or adjusted under 35 U.S.C. 154(b) by 0 days.

(21) Appl. No.: 09/857,983
(22) PCT Filed: Dec. 23, 1998
(86) PCT No.: PCT/US98/27599
§ 371 (c)(1), (2), (4) Date: Jun. 12, 2001
(87) PCT Pub. No.: WO00/38564
PCT Pub. Date: Jul. 6, 2000

(51) Int. Cl.[7] ................................................. B43K 5/14
(52) U.S. Cl. ............................ 401/133; 401/132; 604/3
(58) Field of Search ................................ 401/132, 133, 401/134, 135, 196, 205; 604/3

(56) References Cited

U.S. PATENT DOCUMENTS

| | | | | |
|---|---|---|---|---|
| 4,784,506 A | * | 11/1988 | Koreska et al. ............. | 401/132 |
| 5,509,744 A | * | 4/1996 | Frazier ....................... | 401/132 |
| 5,772,346 A | * | 6/1998 | Edwards ..................... | 401/132 |
| 6,254,297 B1 | * | 7/2001 | Frazier ....................... | 401/133 |

* cited by examiner

Primary Examiner—David J. Walczak
(74) Attorney, Agent, or Firm—Zachary T. Wobensmith, III

(57) ABSTRACT

An applicator for dispensing liquids including an outer tube (11) with at least one layer (39) of impervious plastic thereon, which has a crushable ampoule (20) therein containing the liquid to be dispensed. The outer tube is closed at one end and open at the other with an applicator tip (15) of porous foam thereon. A slide ring activator tool (25) of L-shape is carried on the tube and is rotated to break the ampoule and allow the liquid to flow through the tube to the applicator tip from which it is applied to a surface. The tool has forks (36) that may be moved to extend along each side of the tip to act as a guide for the applicator.

6 Claims, 3 Drawing Sheets

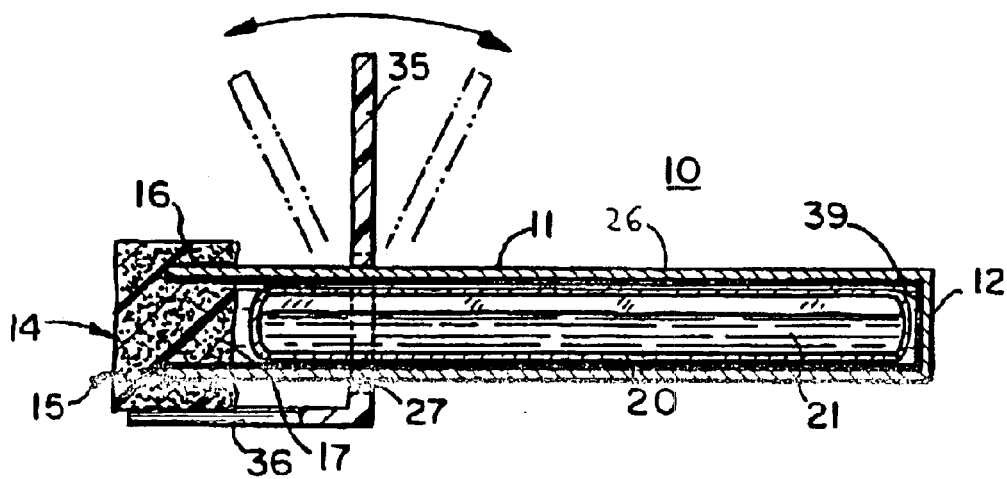
FIG. 4
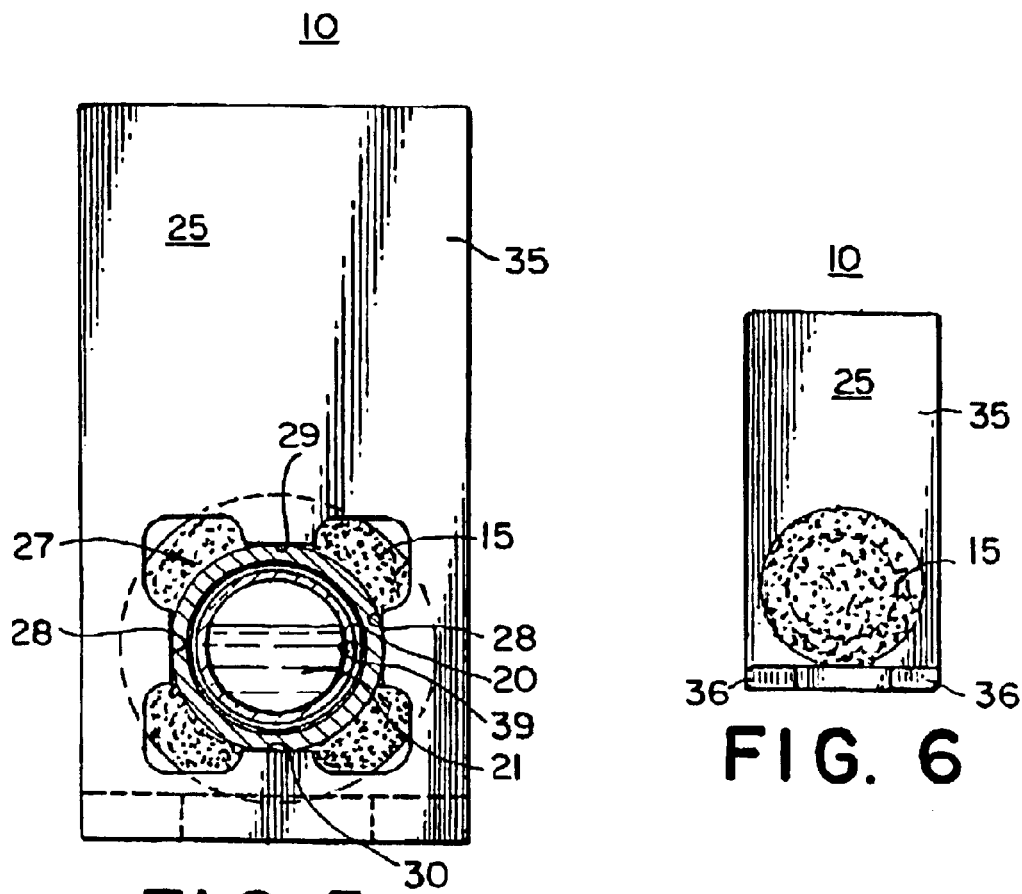
FIG. 5
FIG. 6

LIQUID APPLICATOR WITH SLIDE RING ACTIVATOR TOOL

BACKGROUND OF THE INVENTION

1. Field of the Invention

This invention relates to an applicator of the tubular type, which has a multi-layered cardboard tube, a crushable liquid filled ampoule, a uniquely designed foam tip, and which is activated by an L-shaped slide ring activator tool carried on the outside of the applicator.

2. Description of the Prior Art

Applicators for dispensing liquids, which are of the single use throwaway type are in widespread use.

Many of the applicators contain a glass or plastic liquid filled crushable ampoule, which is encased in a plastic tube that has a porous tip glued to the open end. This inner assembly may also have to be further enclosed in an external cardboard tube to prevent the glass shards from penetrating the inner assembly and cutting the end user when the total package is manually crushed. The seal on the porous tip is critical and must be continuous around the circumference of the tube to prevent the liquid from bypassing the porous tip, and thus creating excessive dripping or excessive flow around the tip. Conventional type applicators, therefore require both an inner plastic tube with a sealed applicator tip and an outer cardboard tube for shard protection.

While the applicators are of many different types and configurations, they must be inexpensive, easy and safe to use, retain the liquid in the container until use, protect the user from contact with the liquid and contact with the broken glass shards generated upon breaking the glass ampoules.

These devices may utilize a lever carried on the container which is rotated to cause the ampoule to break and the liquid to be released for dispensing. As discussed in my prior U.S. Pat. No. 5,509,744, these single lever activators can cause the glass shards to penetrate the tube through the opposite side of the tube. As mentioned above, some of these package devices must rely on an inner and an outer tube to prevent the glass shards from coming through the outer container, which adds to the costs, and are necessary to provide an inner "moisture proof and leak proof" environment for the liquid causing it to exit only through the porous tip.

One example of a slide ring activator type dispenser is disclosed in my prior U.S. Pat. No. 5,509,744, which, while satisfactory, requires a molded two piece plastic outer container which is more expensive to construct, and assemble than the device of the current invention. In addition, the slide ring applicator of my prior patent is limited to one function, i.e., to easily crush the inner ampoule, and it does not have a built in edge guide for guiding its travel while dispensing the liquid.

The liquid applicator of the invention has an outer cardboard tube with an impervious inner layer that is made as part of the tube construction (thus providing a more cost effective solution to the need to provide a separate inner plastic tube to "contain the liquid" within the device after activation). The invention also has a glass ampule therein, which is easily crushed by the L-shaped level type slide activator tool, which tool also acts as an edge guide for the applicator, and which provides many additional advantages. For example, the tool can be removed from the expended applicator after use and reused on a new applicator, thus saving costs. The applicator of the invention also has a uniquely configured porous foam tip. The tip is designed with a partially cut internal ridge that presents a very torturous path for the dispensed liquid to pass, thus preventing the liquid from "short circuiting" the controlled flow of liquid through the porous tip and not going straight down the inside of the tube, which the prior art straight porous tips would allow, causing non uniform liquid application or even drips. This uniquely designed tip could even be used without gluing the tip to the tube, and still provide uniform liquid application if so desired. Finally, the design of the porous tip can easily be increased in diameter to provide for wider liquid application than can conventional "straight plug type tips" without altering the tube diameter or adding an expansion collar to allow for wider tip reconfigurations. Thus, this invention is more easily and less costly to modify to lay down liquid widths.

SUMMARY OF THE INVENTION

This invention relates to a liquid applicator device, which has an outer multilayered cardboard tube with a liquid filled glass ampoule therein. The package device is "sealed" with a specially cut and configured foam tip at the open end of the tube. There is an L-shaped slide ring activator tool carried on the outside of the tube that is rotated to crush the ampoule to release the liquid to be dispensed through the applicator tip. As in my prior invention (U.S. Pat. No. 5,509,744) the crushing action is inwardly directed on two sides of the tube, preventing shards from penetrating the single cardboard tube. The inner wall of the cardboard tube has an impervious layer of thin plastic film or other well known material to prevent the liquid from leaking out of the applicator through the walls of the tube, and directed down toward the porous tip. The tip is constructed with an inner circular ring cut partially through the tip to allow the open end of the tube to properly mate, thereby creating a torturous path for the liquid to follow and to not flow around the tip. The activator tool has edge guide forks adjacent the tip to guide the applicator in use.

The principal object of the invention is to provide a liquid applicator which has an L-shaped slide ring activator tool for one hand operation to crush a liquid filled glass ampoule for liquid dispensing, which tool includes guide forks which act as edge guides for the device.

A further object of the invention is to provide a liquid applicator which is simple and more inexpensive to construct, which is recyclable, and which can be easily modified with wider tips for various width liquid applications, and eliminates the need for a separate inner plastic tube.

A further object of the invention is to provide a liquid applicator which is safe to use.

A further object of the invention is to provide a liquid applicator which is useful to dispense a wide variety of liquid materials.

Other objects and advantageous features of the invention will be apparent from the description and claims.

DESCRIPTION OF THE DRAWINGS

The nature and characteristic features of the invention will be more readily understood from the following description taken in connection with the accompanying drawings forming part hereof in which:

FIG. 4 is a vertical sectional view taken approximately on the line 4—4 of FIG. 2;

FIG. 5 is a vertical sectional view, enlarged, taken approximately on the line 5—5 of FIG. 2;

FIG. 6 is a front end view of the device of FIG. 1;

It should, of course, be understood that the description and drawings herein are merely illustrative, and that various modifications and changes can be made in the structure disclosed without departing from the spirit of the invention.

Like numerals refer to like parts throughout the several views.

DESCRIPTION OF THE PREFERRED EMBODIMENT

When referring to the preferred embodiment, certain terminology will be utilized for the sake of clarity. Use of such terminology is intended to encompass not only the described embodiment, but also technical equivalents which operate and function in substantially the same way to bring about the same result.

Figure 1:
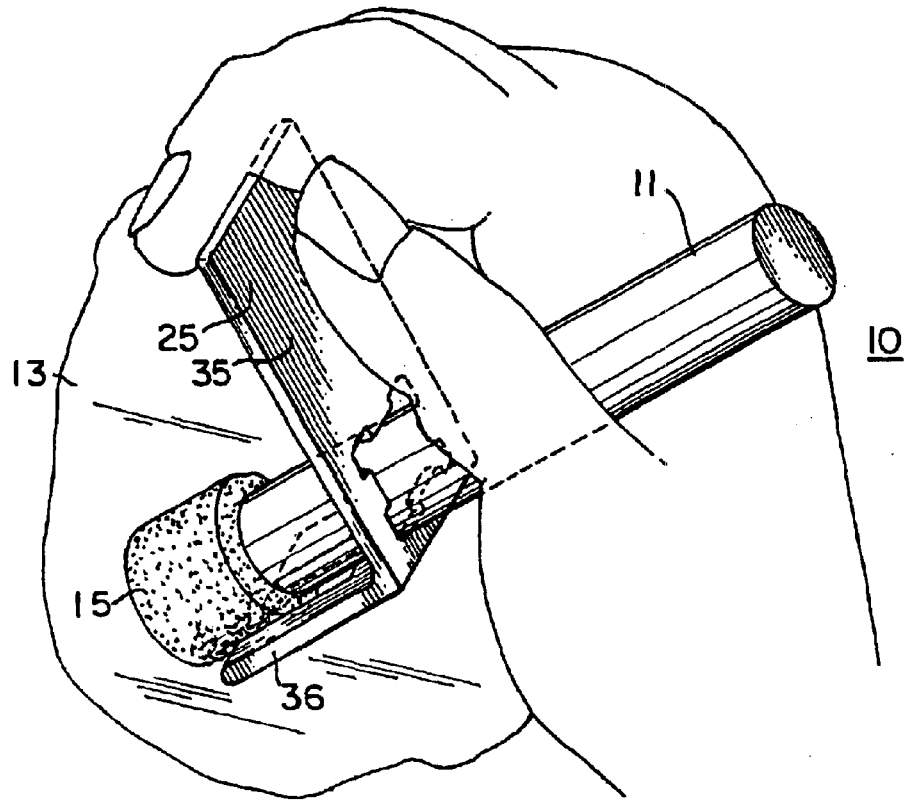
FIG. 1 is a perspective view of the liquid applicator device of the invention.
Figure 2:
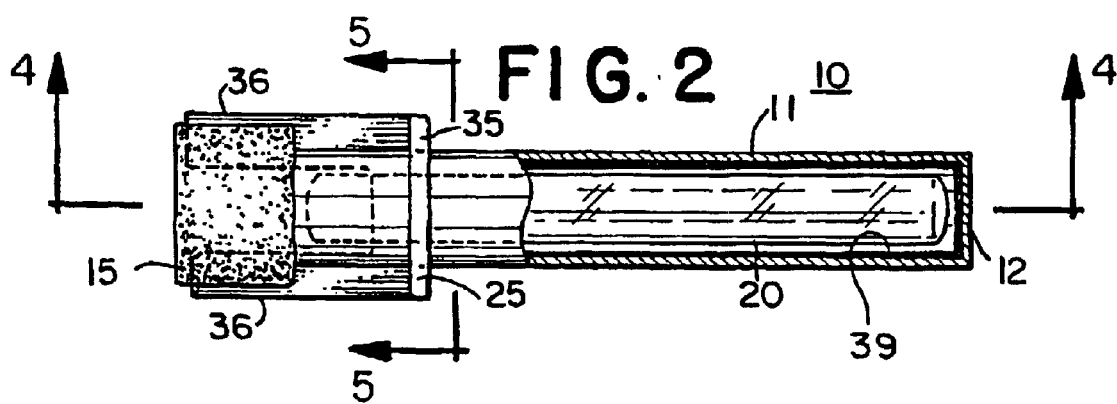
FIG. 2 is a top plan view of the liquid applicator device of FIG. 1 partially broken away to show the interior of the device.
Figure 3:
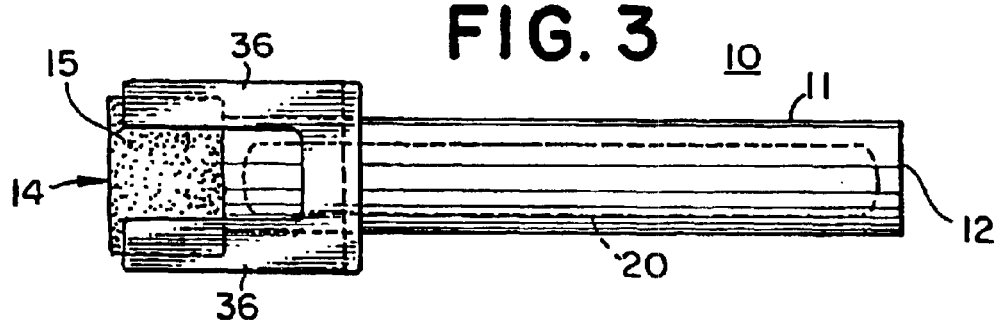
FIG. 3 is a bottom plan view of the device of FIG. 2.
Figure 7:
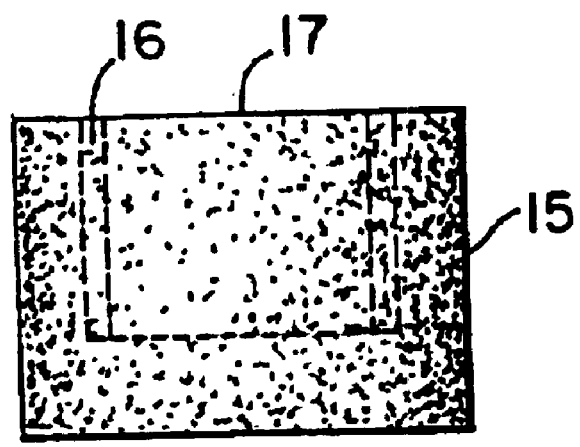
FIG. 7 is a side view of the porous tip of the device.
Figure 8:
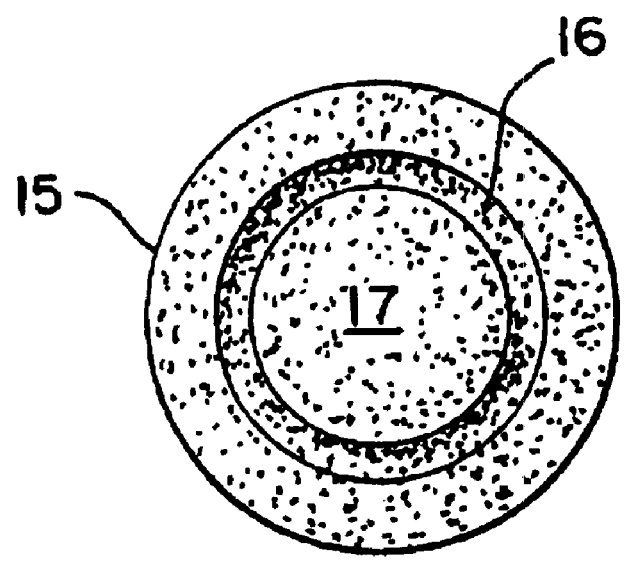
FIG. 8 is a top view of the tip illustrated in FIG. 7.

Referring now more particularly to FIGS. 1–6 of the drawings, the liquid applicator device 10 of the invention is therein illustrated, and in FIG. 1 is shown adjacent to a surface 13 to which liquid is to be applied.

The applicator device 10 includes an outer hollow tube 11, preferably constructed of cardboard, with an inner layer 39 laminated thereto which layer is preferably of polyethylene, which tube is closed at one end 12 and open at end 14. An applicator tip 15 is provided on end 14, which is of a cylindrical shape, with a circular slot 16 into which the tube 11 extends, with a portion 17 of the tip extending into the tube 11. The applicator tip 15 is preferably constructed of plastic foam of well known type, and compatible with the liquid to be dispensed. The tip 15 is secured to tube 11 by adhesive of well known type.

A crushable ampoule 20 is provided within the tube 11, which contains liquid 21 to be dispensed, and which is preferably constructed of glass. The ampoule 20 can be constructed of other suitable material, such as crushable plastic, the selected material being determined by the characteristics of the liquid to be dispensed.

A slide ring activator tool 25 is provided on the outer surface 26 of tube 11, which tool is of 90° L-shape with an interior opening 27, with a pair of side projections 28 in contact with surface 26, and a pair of upper and lower projections 29 and 30 also in contact with surface 26.

The interior opening 27 in tool 25 is greater than the outer diameter of tube 11, and the side projections 28 act as pivots, to be described.

The tool 25 may be formed of any rigid material, nylon being the preferred material.

The upper and lower projections 29 and 30 are intended to be used to crush the ampoule 20, to be described.

The tool 25 has an upper arm 35, which includes the interior opening 27 described above, and has a pair of forks 36 extending forwardly from the bottom end of arm 35 toward the applicator tip 15.

The mode of operation will now be described. The device 10, with tool 25 thereon, is taken to the location where liquid 21 is to be applied.

The applicator 10 as shown in FIGS. 1 and 4 is held in the users hand, the tool 25 rotated by the users fingers about tube 11. The projections 28 act as pivots, and the upper and lower projections 29 and 30 deflect the tube 11 and crush the inner ampoule 20, causing liquid 21 to be released and flow to applicator tip 15. The forces exerted by the tool are always inwardly directed thereby avoiding glass shards from pushing outwardly through the tube 11.

Because the porous tip 15 has a circular cut slot 16, the liquid is forced down and around the entire tip, evenly saturating the total porous tip, and preventing short circuiting of the liquid directly down between the tube and the tip 15, which can happen when the surface tension of the liquid to the inner wall of the tube is such to cause the liquid to travel preferentially straight down the edge of the tube.

The glass shards (not shown) are retained in the tube 11 and do not penetrate the tube. The liquid 21 does not penetrate the tube 11 because of the non porous layer 39.

The tool 25 is preferably rotated with the forks 36 behind tip 15, and after rotation the tool 25 may be slid forwardly until forks 36 are in contact with tip 15. The forks 36 can then be used to position and guide the applicator 10 along the edge of the surface 13 to be treated with the liquid through tip 15, with the result that a continuous border of liquid is applied along the edge of the surface 13. The tool 25 can be saved and reused on other applicators.

Upon finishing the job the applicator device 10 can be recycled and the components reclaimed for use as desired.

It will thus be seen that an applicator has been provided with which the objects of the invention are attained.

I claim:

1. An applicator for selectively dispensing liquids which comprises a hollow tube which is closed at one end and open at the other end, a crushable ampoule in said tube which contains a liquid to be dispensed, an applicator tip on said open end of said tube to receive and to dispense liquid from said ampoule, an L-shaped slide activator tool on said tube, said tool having an interior opening to receive said tube, a pair of side projections in said opening engaging said tube, an upper and a lower projection in said opening engaging said tube, and upon rotation of said tool about said side projections crushing said tube and said ampoule to allow liquid to flow thereout, and to said tip for dispensing.

2. An applicator as defined in claim 1 in which said tube has an inner layer of liquid impervious material to prevent liquid from penetrating the tube walls.

3. An applicator as defined in claim 1 in which said tip has a circular slot to receive said open end of said tube whereby liquid is forced to saturate said tip and is prevented from directly exiting the tube.

4. An applicator as defined in claim 1 in which said tool has an upper arm and at least one fork extending therefrom toward said applicator tip, which fork can be used as an edge guide for said applicator.

5. An applicator as defined in claim 1 in which said ampoule is of glass.

6. An applicator as defined in claim 1 in which said ampoule is of plastic.

* * * * *